(12) United States Patent
Palle et al.

(10) Patent No.: US 7,915,286 B2
(45) Date of Patent: Mar. 29, 2011

(54) SUBSTITUTED PYRAZOLO [3,4-B] PYRIDINES AS PHOSPHODIESTERASE INHIBITORS

(75) Inventors: Venkata P. Palle, Hinjewadi (IN); Sarala Balachandran, Mumbai (IN); Nidhi Gupta, New Delhi (IN); Vinayak Vasantrao Khairnar, Nashik (IN); Mandadapu Raghuramaiah, Guntur (IN); Abhijit Ray, New Delhi (IN); Sunanda Ghose Dastidar, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 374 days.

(21) Appl. No.: 12/067,013

(22) PCT Filed: Sep. 11, 2006

(86) PCT No.: PCT/IB2006/002494
§ 371 (c)(1),
(2), (4) Date: Oct. 23, 2008

(87) PCT Pub. No.: WO2007/031838
PCT Pub. Date: Mar. 22, 2007

(65) Prior Publication Data
US 2009/0306129 A1 Dec. 10, 2009

(30) Foreign Application Priority Data
Sep. 16, 2005 (IN) .......................... 2522/DEL/2005

(51) Int. Cl.
A61K 31/415 (2006.01)
A61K 31/437 (2006.01)
C07D 231/10 (2006.01)
C07D 471/04 (2006.01)
A61P 11/06 (2006.01)
A61P 25/00 (2006.01)
A61P 17/00 (2006.01)
A61P 29/00 (2006.01)
A61P 19/02 (2006.01)

(52) U.S. Cl. ...... 514/303; 514/406; 546/120; 548/375.1
(58) Field of Classification Search ............... 514/303, 514/406; 546/120; 548/375.1
See application file for complete search history.

(56) References Cited

U.S. PATENT DOCUMENTS

| | | |
|---|---|---|
| 3,312,590 A | 4/1967 | Elks et al. |
| 3,436,389 A | 4/1969 | Giangiacomo et al. |
| 3,506,694 A | 4/1970 | Oxley et al. |
| 3,639,434 A | 2/1972 | Oxley et al. |
| 3,642,896 A | 2/1972 | Collin et al. |
| 3,644,353 A | 2/1972 | Lunts et al. |
| 3,652,554 A | 3/1972 | Anner et al. |
| 3,700,681 A | 10/1972 | Barth |
| 3,705,233 A | 12/1972 | Lunts et al. |
| 3,721,687 A | 3/1973 | Elks et al. |
| 3,780,177 A | 12/1973 | Ercoli et al. |
| 3,928,326 A | 12/1975 | Brattsand et al. |
| 3,929,768 A | 12/1975 | Brattsand et al. |
| 3,937,838 A | 2/1976 | Wetterlin et al. |
| 3,947,478 A | 3/1976 | Woods et al. |
| 3,980,778 A | 9/1976 | Ayer et al. |
| 3,983,233 A | 9/1976 | Brattsand et al. |
| 3,992,534 A | 11/1976 | Brattsand et al. |
| 3,994,974 A | 11/1976 | Murakami et al. |
| 4,011,258 A | 3/1977 | Wetterlin et al. |
| 4,014,909 A | 3/1977 | Torossian et al. |
| 4,076,708 A | 2/1978 | Green et al. |
| 4,081,541 A | 3/1978 | Bertelli |
| 4,098,803 A | 7/1978 | Torossian et al. |
| 4,124,707 A | 11/1978 | Green et al. |
| 4,158,055 A | 6/1979 | Shultz et al. |
| 4,226,862 A | 10/1980 | Riva et al. |
| 4,242,334 A | 12/1980 | Stache et al. |
| 4,290,962 A | 9/1981 | Tachi et al. |
| 4,298,604 A | 11/1981 | Hammell et al. |
| 4,335,121 A | 6/1982 | Phillipps et al. |
| 4,419,364 A | 12/1983 | Olsson et al. |
| 4,472,392 A | 9/1984 | Anderson et al. |
| 4,579,985 A | 4/1986 | Minderhoud et al. |
| 4,587,236 A | 5/1986 | Annen et al. |
| 4,619,921 A | 10/1986 | Kalvoda et al. |

(Continued)

FOREIGN PATENT DOCUMENTS
EP 0 068 806 1/1983
(Continued)

OTHER PUBLICATIONS

Sutherland and Rall, "The Relation of Adenosine-3', 5'-Phosphate and Phosphorylase to the Actions of Catecholamines and Other Hormones", *Pharmacological Reviews*, 12(3):265-299 (1960).

(Continued)

*Primary Examiner* — D. Margaret Seaman
*Assistant Examiner* — Niloofar Rahmani

(57) ABSTRACT

The present invention relates to phosphodiesterase (PDE) type IV selective inhibitors. Processes for the preparation of disclosed compounds, pharmaceutical compositions containing the disclosed compounds and their use as PDE type IV selective inhibitors are provided. Prepared compounds correspond to structure XIV Formula (XIV).

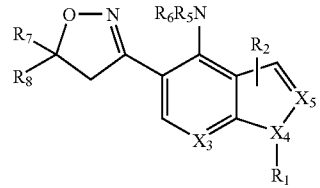

5 Claims, No Drawings

U.S. PATENT DOCUMENTS

| | | | |
|---|---|---|---|
| 4,780,469 A | 10/1988 | Toda et al. | |
| 4,826,868 A | 5/1989 | Wachter et al. | |
| 4,859,692 A | 8/1989 | Bernstein et al. | |
| 4,873,259 A | 10/1989 | Summers, Jr. et al. | |
| 4,992,474 A | 2/1991 | Skidmore et al. | |
| 5,015,746 A | 5/1991 | Mizushima et al. | |
| 5,126,375 A | 6/1992 | Skidmore et al. | |
| 5,243,076 A | 9/1993 | Skidmore et al. | |
| 5,278,156 A | 1/1994 | Mizushima et al. | |
| 5,482,934 A | 1/1996 | Calatayud et al. | |
| 5,565,473 A | 10/1996 | Belley et al. | |
| 5,583,152 A | 12/1996 | Bernstein et al. | |
| 5,837,699 A | 11/1998 | Sequeira et al. | |
| 5,889,015 A | 3/1999 | Sequeira et al. | |
| 5,976,573 A | 11/1999 | Kim | |
| 6,057,307 A | 5/2000 | Sequeira et al. | |
| 6,107,301 A | 8/2000 | Aldrich et al. | |
| 6,127,353 A | 10/2000 | Yuen et al. | |
| 6,180,781 B1 | 1/2001 | Yuen et al. | |
| 6,337,324 B1 | 1/2002 | Harmenberg et al. | |
| 6,339,099 B1 | 1/2002 | Lam et al. | |
| 6,723,713 B2 | 4/2004 | Sequeira et al. | |
| 2003/0176421 A1 | 9/2003 | Watson et al. | |
| 2004/0167030 A1 | 8/2004 | Bernotas et al. | |
| 2004/0176325 A1 | 9/2004 | Munson et al. | |
| 2004/0180896 A1 | 9/2004 | Munson et al. | |
| 2004/0192653 A1 | 9/2004 | Munson et al. | |
| 2005/0208582 A1 | 9/2005 | Ohi et al. | |
| 2010/0292196 A1* | 11/2010 | Rudra et al. | 514/171 |

FOREIGN PATENT DOCUMENTS

| | | |
|---|---|---|
| EP | 0 542 356 | 11/1991 |
| EP | 0 542 355 | 5/1993 |
| EP | 0 419 049 | 4/1995 |
| EP | 0 773 023 | 5/1997 |
| EP | 1 040 829 | 10/2000 |
| EP | 1 040 831 | 10/2000 |
| EP | 1 059 100 | 12/2000 |
| EP | 1 097 709 | 5/2001 |
| EP | 1 149 583 | 10/2001 |
| EP | 1 251 128 | 10/2002 |
| WO | WO 93/05021 | 3/1993 |
| WO | WO 95/10506 | 4/1995 |
| WO | WO 95/34563 | 12/1995 |
| WO | WO 97/48697 | 12/1997 |
| WO | WO 97/49702 | 12/1997 |
| WO | WO 98/09961 | 3/1998 |
| WO | WO 98/57951 | 12/1998 |
| WO | WO 99/23076 | 5/1999 |
| WO | WO 99/23077 | 5/1999 |
| WO | WO 00/15222 | 3/2000 |
| WO | WO 00/42045 | 7/2000 |
| WO | WO 00/59902 | 10/2000 |
| WO | WO 01/19798 | 3/2001 |
| WO | WO 01/23389 | 4/2001 |
| WO | WO 01/58489 | 8/2001 |
| WO | WO 02/18383 | 3/2002 |
| WO | WO 02/22604 | 3/2002 |
| WO | WO 02/22606 | 3/2002 |
| WO | WO 02/24694 | 3/2002 |
| WO | WO 02/50070 | 6/2002 |
| WO | WO 02/051832 | 7/2002 |
| WO | WO 02/051837 | 7/2002 |
| WO | WO 02/060900 | 8/2002 |
| WO | WO 02/081463 | 10/2002 |
| WO | WO 03/024969 | 3/2003 |
| WO | WO 03/047520 | 6/2003 |
| WO | WO 03/064397 | 8/2003 |
| WO | WO 03/068773 | 8/2003 |
| WO | WO 2004/009600 | 1/2004 |
| WO | WO 2004/014368 | 2/2004 |
| WO | WO 2004/024728 | 3/2004 |
| WO | WO 2004/028481 | 4/2004 |
| WO | WO 2004/037814 | 5/2004 |
| WO | WO 2004/056823 | 7/2004 |
| WO | WO 2004/076450 | 9/2004 |
| WO | WO 2004/080463 | 9/2004 |
| WO | WO 2004/096130 | 11/2004 |
| WO | WO 2004/108133 | 12/2004 |
| WO | WO 2005/009389 | 2/2005 |
| WO | WO 2005/009958 | 2/2005 |
| WO | WO 2005/021515 | 3/2005 |
| WO | WO 2005/028480 | 3/2005 |
| WO | WO 2005/058892 | 6/2005 |
| WO | WO 2005/063767 | 7/2005 |
| WO | WO 2005/077955 | 8/2005 |
| WO | WO 2005/082367 | 9/2005 |
| WO | WO 2005/085248 | 9/2005 |
| WO | WO 2005/085249 | 9/2005 |
| WO | WO 2005/100353 | 10/2005 |
| WO | WO 2005/111038 | 11/2005 |
| WO | WO 2006/001894 | 1/2006 |
| WO | WO 2006/004188 | 1/2006 |
| WO | WO 2006/009245 | 1/2006 |
| WO | WO 2006/013095 | 2/2006 |
| WO | WO 2006/023704 | 3/2006 |
| WO | WO 2006/046023 | 5/2006 |
| WO | WO 2006/047415 | 5/2006 |
| WO | WO 2006/047516 | 5/2006 |
| WO | WO 2006/050076 | 5/2006 |
| WO | WO 2006/050109 | 5/2006 |
| WO | WO 2006/058074 | 6/2006 |
| WO | WO 2006/058120 | 6/2006 |
| WO | WO 2006/060456 | 6/2006 |
| WO | WO 2006/060535 | 6/2006 |

OTHER PUBLICATIONS

Beavo and Reifsnyder, "Primary Sequence of Cyclic Nucleotide Phosphodiesterase Isozymes and the Design of Selective Inhibitors", *Trends in Pharmacological Sciences*, 11(4):150-155 (1990).

Nicholson et al., "Differential Modulation of Tissue Function and Therapeutic Potential of Selective Inhibitors of Cyclic Nucleotide Phosphodiesterase Isoenzymes", *Trends in Pharmacological Sciences*, 12:19-27 (1991).

Verghese et al., "Anti-Neutrophil Activity of Cyclic Nucleotide Phosphodiesterase Inhibitors with Varying Cardiotonic Potencies", *Journal of Molecular and Cellular Cardiology*, 12(Suppl. II):S61 (1989).

Zhang et al., "Phosphodiesterase-4 as a Potential Drug Target", *Expert Opinion on Therapeutic Targets*, 9(6):1283-1305 (2005).

Houslay et al., "Keynote Review: Phosphodiesterase-4 as a therapeutic target", *Drug Discovery Today*, 10(22):1503-1519 (2005).

Lambrecht et al., "Pharmacology of Hexahydro-Difenidol, Hexahydro-sila-Difenidol and Related Selective Muscarinic Antagonists", *Trends in Pharmacol. Sci.*, 10(Suppl):60-64 (1989).

Birdsall et al., "Muscarinic Receptor Subclasses", *Trends in Pharmacol. Sci.*, 4:459 (1983).

Coruzzi et al., "Gastric Antisecretory Activity of Telenzepine, a New $M_1$-Selective Muscarinic With Pirenzepine", *Arch. Int. Pharmacodyn. Ther.*, 302:232-241 (1989).

Kawashima et al., "Pharmacological Differentiation of Presynaptic M1 Muscarinic Receptors Modulating Acetylcholine Release From Postsynaptic Muscarinic Receptors in Guinea-Pig Ileum", *Gen. Pharmacol.*, 21(1):17-21 (1990).

DiSanto, et al., "Identification and Stabilization of Large Molecular Weight PDE-Ivs From U937 Cells", *Biochem. Biophys. Res. Comm.*, 197(3):1126-1131 (1993).

\* cited by examiner

SUBSTITUTED PYRAZOLO [3,4-B] PYRIDINES AS PHOSPHODIESTERASE INHIBITORS

FIELD OF THE INVENTION

The present invention relates to phosphodiesterase (PDE) type IV selective inhibitors.

Compounds disclosed herein can be useful in the treatment of CNS diseases, AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases especially in humans.

Processes for the preparation of disclosed compounds, pharmaceutical compositions containing the disclosed compounds and their use as PDE type IV selective inhibitors are provided.

BACKGROUND OF THE INVENTION

It is known that cyclic adenosine-3',5'-monophosphate (cAMP) exhibits an important role of acting as an intracellular secondary messenger (E. W. Sutherland, and T. W. Roll, *Pharmacol. Rev.*, (1960), 12, 265). Its intracellular hydrolysis to adenosine 5'-monophosphate (AMP) causes number of inflammatory conditions which are not limited to psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis. PDE4 inhibitors are designed to inhibit the activity of PDE4, the enzyme which breaks down neuronal cAMP. Studies have shown that administering PDE4 inhibitors can have a restorative effect on memory loss in animal models, including those of Alzheimer's disease (*Expert Opin. Ther. Targets*, (2005) 9(6):1283-1305; *Drug Disc. Today*, 10, (2005)). The most important role in the control of cAMP (as well as of cGMP) level is played by cyclic nucleotide phosphodiesterases (PDE) which represent a biochemically and functionally highly variable super family of enzymes. Eleven distinct families of cyclic nucleotide phosphodiesterases with more than 25 gene products are currently recognized. Although PDE I, PDE II, PDE III, PDE IV, and PDE VII all use cAMP as a substrate, only PDE IV and PDE VII are highly selective for hydrolysis of cAMP. Inhibitors of PDE, particularly the PDE IV inhibitors, such as rolipram or Ro-1724 are therefore known as cAMP-enhancers. Immune cells contain type IV and type III PDE, the PDE IV type being prevalent in human mononuclear cells. Thus the inhibition of phosphodiesterase type IV has been a target for modulation and, accordingly, for therapeutic intervention in a range of disease processes.

The initial observation that xanthine derivatives, theophylline and caffeine inhibit the hydrolysis of cAMP led to the discovery of the required hydrolytic activity in the cyclic nucleotide phosphodiesterase (PDE) enzymes. Distinct classes of PDE's have been recognized (Bervo et al., *TIPS*, (1990), 11, 150), and their selective inhibition has led to improved drug therapy (Nicholus et al., *TIPS*, (1991), 12, 19). Thus it was recognized that inhibition of PDE IV could lead to inhibition of inflammatory mediator release (Verghese et al., *J. Mol. Cell. Cardio.*, (1989), 12 (Suppl. II), S 61) and airway smooth muscle relaxation.

WO 2003/047520 discloses substituted aminomethyl compounds and derivatives thereof, which have been described to be useful as inhibitors of factor Xa. WO 2000/59902 discloses aryl sulfonyls, which have been described to be useful as inhibitors of factor Xa. WO 97/48697 discloses substituted azabicyclic compounds and their reported use as inhibitors of the production of TNF and cyclic AMP phosphodiesterase. WO 98/57951 and U.S. Pat. No. 6,339,099 describe nitrogen containing heteroaromatics and derivatives, which have been said to be inhibitors of factor Xa. WO 01/19798 discloses compounds, which have been described to have activity against mammalian factor Xa.

SUMMARY OF THE INVENTION

Herein are provided phosphodiesterase (PDE) type IV selective inhibitors, which can be used for the treatment of CNS diseases, AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases and the processes for the synthesis of these compounds.

Pharmaceutically acceptable salts, pharmaceutically acceptable solvates, stereoisomers, tautomers, racemates, regioisomers, prodrugs, metabolites, polymorphs or N-oxides of these compounds having the same type of activity are also provided.

Pharmaceutical compositions containing the compounds are provided, which may also contain pharmaceutically acceptable carriers or diluents, and which can be used for the treatment of CNS diseases, AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases.

Other aspects will be set forth in the accompanying description which follows and in part will be apparent from the description or may be learnt by the practice of the invention.

In accordance with one aspect, there are provided compounds having the structure of Formula I:

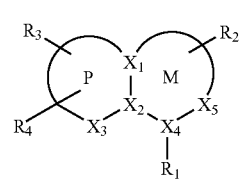

Formula I and their pharmaceutically acceptable salts, pharmaceutically acceptable solvates, stereoisomers, tautomers, racemates, regioisomers, prodrugs, metabolites, polymorphs or N-oxides, wherein ring P including $X_1$, $X_2$ and $X_3$ can be a six-membered ring containing 1-3 double bonds wherein $X_1$ and $X_2$ can be carbon and $X_3$ can be nitrogen;

ring M including $X_1$, $X_2$, $X_4$ and $X_5$ can be a five-membered ring containing 1-2 double bonds wherein $X_1$ and $X_2$ can be carbon and $X_4$ and $X_5$ can be nitrogen;

$R_1$ can be hydrogen, alkyl, alkenyl, alkynyl, cycloalkyl, aryl, aralkyl, aralkenyl, (cycloalkyl) alkyl, heterocyclyl, heteroaryl, (heterocyclyl) alkyl or (heteroaryl) alkyl;

$R_2$ can be hydrogen, alkyl, halogen, cyano, nitro, —SR, NRR, —$(CH_2)_n$OR {wherein R can be hydrogen, alkyl, alkenyl, alkynyl, cycloalkyl, aryl, heteroaryl or heterocyclyl and n can be an integer from 0-2}, alkenyl, alkynyl, cycloalkyl, (cycloalkyl) alkyl, aryl, aralkyl, aralkenyl, heterocyclyl, heteroaryl, (heterocyclyl) alkyl or (heteroaryl) alkyl;

$R_3$ can be $-NR_5R_6$ {wherein $R_5$ and $R_6$ independently can be hydrogen, alkyl, alkenyl, alkynyl, acyl, cycloalkyl, aryl, aralkenyl, aralkyl, (cycloalkyl) alkyl, heterocyclyl, heteroaryl, (heterocyclyl) alkyl or (heteroaryl) alkyl}; and $R_4$ can be a radical of Formula I a or I b

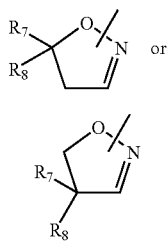

Formula Ia

Formula Ib wherein $R_7$ and $R_8$ independently can be allyl, $-CN$, $-(CH_2)_nC(=O)NR_fR_q$ {wherein n can be an integer from 0-2 and $R_f$ and $R_q$ independently can be hydrogen, alkyl, alkenyl, cycloalkyl, aryl, aralkyl, heterocyclyl, heteroaryl, (heterocyclyl)alkyl, (heteroaryl)alkyl}, $-(CH_2)_nC(=O)OR_f$ {wherein n and $R_f$ are the same as defined earlier}, $-(CH_2)_nOR_f$ {wherein n and $R_f$ are the same as defined earlier}.

The following definitions apply to terms as used herein.

The term "alkyl," unless otherwise specified, refers to a monoradical branched or unbranched saturated hydrocarbon chain having from 1 to 20 carbon atoms. Alkyl groups can be optionally interrupted by atom(s) or group(s) independently selected from oxygen, sulfur, a phenylene, sulphinyl, sulphonyl group or $-NR_\alpha-$, wherein $R_\alpha$ can be hydrogen, alkyl, cycloalkyl, alkenyl, cycloalkenyl, alkynyl, aryl, acyl, aralkyl, $-C(=O)OR_\lambda$, $SO_mR_\psi$, or $-C(=O)NR_\lambda R_\pi$. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, tetradecyl, and the like. Alkyl groups may be substituted further with one or more substituents selected from alkenyl, alkynyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, aryl, heterocyclyl, heteroaryl, (heterocyclyl)alkyl, cycloalkoxy, $-CH=N-O(C_{1-6}alkyl)$, $-CH=N-NH(C_{1-6}alkyl)$, $-CH=N-NH(C_{1-6}alkyl)-C_{1-6}alkyl$, arylthio, thiol, alkylthio, aryloxy, nitro, aminosulfonyl, aminocarbonylamino, $-NHC(=O)R_\lambda$, $-NR_\lambda R_\pi$, $-C(=O)NR_\lambda R_\pi$, $-NHC(=O)NR_\lambda R_\pi$, $-C(=O)heteroaryl$, $C(=O)heterocyclyl$, $-O-C(=O)NR_\lambda R_\pi$ {wherein $R_\lambda$ and $R_\pi$ are independently selected from hydrogen, halogen, hydroxy, alkyl, alkenyl, alkynyl, alkenyl, alkoxy, cycloalkyl, cycloalkenyl, aryl, aralkyl, heterocyclyl, heteroaryl, heterocyclylalkyl, heteroarylalkyl or carboxy}, nitro or $-SO_mR_\psi$ (wherein m is an integer from 0-2 and $R_\psi$ is hydrogen, alkyl, alkenyl, alkynyl, cycloalkyl, aralkyl, aryl, heterocyclyl, heteroaryl, heteroarylalkyl or heterocyclylalkyl). Unless otherwise constrained by the definition, alkyl substituents may be further substituted by 1-3 substituents selected from alkyl, alkenyl, alkynyl, carboxy, $-NR_\lambda R_\pi$, $-C(=O)NR_\lambda R_\pi$, $-OC(=O)NR_\lambda R_\pi$, $-NHC(=O)NR_\lambda R_\pi$, hydroxy, alkoxy, halogen, $CF_3$, cyano, and $-SO_mR_\psi$; or an alkyl group also may be interrupted by 1-5 atoms of groups independently selected from oxygen, sulfur or $-NR_\alpha-$ (wherein $R_\alpha$, $R_\lambda$, $R_\pi$, m and $R_\psi$ are the same as defined earlier). Unless otherwise constrained by the definition, all substituents may be substituted further by 1-3 substituents selected from alkyl, alkenyl, alkynyl, carboxy, carboxyalkyl, $-NR_\lambda R_\pi$, $-C(=O)NR_\lambda R_\pi$, $-O-C(=O)NR_\lambda R_\pi$, hydroxy, alkoxy, halogen, $CF_3$, cyano, and $-SO_mR_\psi$ (wherein $R_\lambda$, $R_\pi$, m and $R_\psi$ are the same as defined earlier); or an alkyl group as defined above that has both substituents as defined above and is also interrupted by 1-5 atoms or groups as defined above.

The term "alkenyl," unless otherwise specified, refers to a monoradical of a branched or unbranched unsaturated hydrocarbon group having from 2 to 20 carbon atoms with cis, trans or geminal geometry. Alkenyl groups can be optionally interrupted by atom(s) or group(s) independently chosen from oxygen, sulfur, phenylene, sulphinyl, sulphonyl and $-NR_\alpha-$ (wherein $R_\alpha$ is the same as defined earlier). In the event that alkenyl is attached to a heteroatom, the double bond cannot be alpha to the heteroatom. Alkenyl groups may be substituted further with one or more substituents selected from alkyl, alkenyl, alkynyl, alkoxy, cycloalkyl, cycloalkenyl, acyl, acylamino, acyloxy, $-NHC(=O)R_\lambda$, $-NR_\lambda R_\pi$, $-C(=O)NR_\lambda R_\pi$, $-NHC(=O)NR_\lambda R_\pi$, $-O-C(=O)NR_\lambda R_\pi$, alkoxycarbonylamino, azido, cyano, halogen, hydroxy, oxo, keto, carboxyalkyl, thiocarbonyl, carboxy, arylthio, thiol, alkylthio, aryl, aralkyl, aryloxy, heterocyclyl, heteroaryl, heterocyclyl alkyl, heteroaryl alkyl, aminosulfonyl, aminocarbonylamino, alkoxyamino, hydroxyamino, alkoxyamino, nitro or $SO_mR_\psi$ (wherein $R_\lambda$, $R_\pi$, m and $R_\psi$ are as defined earlier). Unless otherwise constrained by the definition, alkenyl substituents optionally may be substituted further by 1-3 substituents selected from alkyl, alkenyl, alkynyl, carboxy, hydroxy, alkoxy, halogen, $-CF_3$, cyano, $-NR_\lambda R_\pi$, $-C(=O)NR_\lambda R_\pi$, $-O-C(=O)NR_\lambda R_\pi$, and $-SO_mR_\psi$ (wherein $R_\lambda R_\pi$, m and $R_\psi$ are as defined earlier). Groups, such as ethenyl or vinyl ($CH=CH_2$), 1-propylene or allyl ($-CH_2CH=CH_2$), iso-propylene ($-C(CH_3)=CH_2$), bicyclo[2.2.1]heptene, and the like, exemplify this term.

The term "alkynyl," unless otherwise specified, refers to a monoradical of an unsaturated hydrocarbon, having from 2 to 20 carbon atoms. Alkynyl groups can be optionally interrupted by atom(s) or group(s) independently chosen from oxygen, sulfur, phenylene, sulphinyl, sulphonyl and $-NR_\alpha-$ (wherein $R_\alpha$ is the same as defined earlier). In the event that alkynyl groups are attached to a heteroatom, the triple bond cannot be alpha to the heteroatom. Alkynyl groups may be substituted further with one or more substituents selected from alkyl, alkenyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, arylthio, thiol, alkylthio, aryl, aralkyl, aryloxy, aminosulfonyl, aminocarbonylamino, hydroxyamino, alkoxyamino, nitro, heterocyclyl, heteroaryl, heterocyclylalkyl, heteroarylalkyl, $-NHC(=O)R_\lambda$, $-NR_\lambda R_\pi$, $-NHC(=O)NR_\lambda R_\pi$, $-C(=O)NR_\lambda R_\pi$, $-O-C(=O)NR_\lambda R_\pi$ or $-SO_mR_\psi$ (wherein $R_\lambda$, $R_\pi$, m and $R_\psi$ are the same as defined earlier). Unless otherwise constrained by the definition, alkynyl substituents optionally may be substituted further by 1-3 substituents selected from alkyl, alkenyl, alkynyl, carboxy, carboxyalkyl, hydroxy, alkoxy, halogen, $CF_3$, $-NR_\lambda R_\pi$, $-C(=O)NR_\lambda R_\pi$, $-NHC(=O)NR_\lambda R_\pi$, $-C(=O)NR_\lambda R_\pi$, cyano or $-SO_mR_\psi$ (wherein $R_\lambda$, $R_\pi$, m and $R_\psi$ are the same as defined earlier).

The term "cycloalkyl," unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclooctyl, cyclopentenyl, and the like or multiple ring structures, including adamantanyl, and bicyclo[2.2.1]heptane or cyclic alkyl groups to which is fused an aryl group, for example, indane, and the like. Spiro and fused ring structures can also be included. Cycloalkyl groups may be substituted further with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, arylthio, thiol, alkylthio, aryl, aralkyl, aryloxy, aminosulfonyl, aminocarbonylamino, —$NR_\lambda R_\pi$, —$NHC(=O)NR_\lambda R_\pi$, —$NHC(=O)R_\lambda$, —$C(=O)NR_\lambda R_\pi$, —O—$C(=O)NR_\lambda R_\pi$, nitro, heterocyclyl, heteroaryl, heterocyclylalkyl, heteroarylalkyl or $SO_m R_\psi$ (wherein $R_\lambda$, $R_\pi$, m and $R_\psi$ are the same as defined earlier). Unless otherwise constrained by the definition, cycloalkyl substituents optionally may be substituted further by 1-3 substituents selected from alkyl, alkenyl, alkynyl, carboxy, hydroxy, alkoxy, halogen, $CF_3$, —$NR_\lambda R_\pi$, —$C(=O)NR_\lambda R_\pi$, —$NHC(=O)NR_\lambda R_\pi$, —$OC(=O)NR_\lambda R_\pi$, cyano or —$SO_m R_\psi$ (wherein $R_\lambda$, $R_\pi$, m and $R_\psi$ are the same as defined earlier). "Cycloalkylalkyl" refers to alkyl-cycloalkyl group linked through alkyl portion, wherein the alkyl and cycloalkyl are the same as defined earlier.

The term "(cycloalkyl) alkyl" refers to alkyl-cycloalkyl group linked through alkyl portion, wherein the alkyl and cycloalkyl are as defined earlier.

The term "alkoxy" denotes the group O-alkyl wherein alkyl is the same as defined above.

The term "aryl," unless otherwise specified, refers to aromatic system having 6 to 14 carbon atoms, wherein the ring system can be mono-, bi- or tricyclic and are carbocyclic aromatic groups. For example, aryl groups include, but are not limited to, phenyl, biphenyl, anthryl or napthyl ring and the like, optionally substituted with 1 to 3 substituents selected from halogen (e.g., F, Cl, Br, I), hydroxy, alkyl, alkenyl, alkynyl, cycloalkyl, alkoxy, acyl, aryloxy, $CF_3$, cyano, nitro, $COOR_\psi$, N—$HC(=O)R_\lambda$, —$NR_\lambda R_\pi$, —$C(=O)NR_\lambda R_\pi$, —$NHC(=O)NR_\lambda R_\pi$, —O—$C(=O)NR_\lambda R_\pi$, —$SO_m R_\psi$, carboxy, heterocyclyl, heteroaryl, heterocyclylalkyl, heteroarylalkyl or amino carbonyl amino, mercapto, haloalkyl, optionally substituted aryl, optionally substituted heterocyclylalkyl, thioalkyl, —$CONHR_\pi$, —$OCOR_\pi$, —$COR_\pi$, —$NHSO_2 R_\pi$, or —$SO_2 NHR_\pi$ (wherein $R_\lambda$, $R_\pi$, m and $R_\psi$ are the same as defined earlier). Aryl groups optionally may be fused with a cycloalkyl group, wherein the cycloalkyl group may optionally contain heteroatoms selected from O, N or S. Groups such as phenyl, naphthyl, anthryl, biphenyl, and the like exemplify this term.

The term "aralkyl," unless otherwise specified, refers to alkyl-aryl linked through an alkyl portion (wherein alkyl is as defined above) and the alkyl portion contains 1-6 carbon atoms and aryl is as defined below. Examples of aralkyl groups include benzyl, ethylphenyl, propylphenyl, naphthylmethyl and the like.

The term "aralkenyl," unless otherwise specified, refers to alkenyl-aryl linked through alkenyl (wherein alkenyl is as defined above) portion and the alkenyl portion contains 1 to 6 carbon atoms and aryl is as defined below.

The term "aryloxy" denotes the group O-aryl, wherein aryl is as defined above.

The term "cycloalkoxy" denotes the group O-cycloalkyl, wherein cycloalkyl is as defined above.

The term "carboxy," as defined herein, refers to —$C(=O)OR_f$, wherein $R_f$ is the same as defined above.

The term "heteroaryl," unless otherwise specified, refers to an aromatic ring structure containing 5 or 6 ring atoms or a bicyclic or tricyclic aromatic group having from 8 to 10 ring atoms, with one or more heteroatom(s) independently selected from N, O or S optionally substituted with 1 to 4 substituent(s) selected from halogen (e.g., F, Cl, Br, I), hydroxy, alkyl, alkenyl, alkynyl, cycloalkyl, acyl, carboxy, aryl, alkoxy, aralkyl, cyano, nitro, heterocyclyl, heteroaryl, —$NR_\lambda R_\pi$, CH=NOH, —$(CH_2)_w C(=O)R_\eta$, {wherein w is an integer from 0-4 and $R_\eta$, is hydrogen, hydroxy, $OR_\lambda$, $NR_\lambda R_\pi$, —$NHOR_\omega$ or —NHOH}, —$C(=O)NR_\lambda R_\pi$, —$NHC(=O)NR_\lambda R_\pi$, —$SO_m R_\psi$, —O—$C(=O)NR_\lambda R_\pi$, —O—$C(=O)R_\lambda$, or —O—$C(=O)OR_\lambda$ (wherein m, $R_\psi$, $R_\lambda$ and $R_\pi$ are as defined earlier and $R_\omega$, is alkyl, cycloalkyl, aryl, heteroaryl, heterocyclyl, heteroarylalkyl or heterocyclylalkyl). Unless otherwise constrained by the definition, the substituents are attached to a ring atom, i.e., carbon or heteroatom in the ring. Examples of heteroaryl groups include oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, pyrazinyl, thienyl, isoxazolyl, triazinyl, furanyl, benzofuranyl, indolyl, benzthiazinyl, benzthiazinonyl, benzoxazinyl, benzoxazinonyl, quinazonyl, carbazolyl phenothiazinyl, phenoxazinyl, benzothiazolyl or benzoxazolyl, and the like.

The term "heterocyclyl," unless otherwise specified, refers to a non-aromatic monocyclic or bicyclic cycloalkyl group having 5 to 10 atoms wherein 1 to 4 carbon atoms in a ring are replaced by heteroatoms selected from O, S or N, and optionally are benzofused or fused heteroaryl having 5-6 ring members and/or optionally are substituted, wherein the substituents are selected from halogen (e.g., F, Cl, Br, I), hydroxy, alkyl, alkenyl, alkynyl, cycloalkyl, acyl, optionally substituted aryl, alkoxy, alkaryl, cyano, nitro, oxo, carboxy, optionally substituted heterocyclyl, optionally substituted heterocyclylalkyl, optionally substituted heteroaryl, —O—$C(=O)R_\lambda$, —O—$C(=O)OR_\lambda$, —$C(=O)NR_\lambda R_\pi$, $SO_m R_\psi$, —O—C($=O)NR_\lambda R_\pi$, —$NHC(=O)NR_\lambda R_\pi$, —$NR_\lambda R_\pi$, mercapto, haloalkyl, thioalkyl, —$COOR_\psi$, —$COONHR_\lambda$, —$COR_\lambda$, —$NHSO_2 R_\lambda$ or $SO_2 NHR_\lambda$ (wherein m, $R_\psi$, $R_\lambda$ and $R_\pi$ are as defined earlier) or guanidine. Heterocyclyl can optionally include rings having one or more double bonds. Such ring systems can be mono-, bi- or tricyclic. Carbonyl or sulfonyl group can replace carbon atom(s) of heterocyclyl. Unless otherwise constrained by the definition, the substituents are attached to the ring atom, i.e., carbon or heteroatom in the ring. Also, unless otherwise constrained by the definition, the heterocyclyl ring optionally may contain one or more olefinic bond(s). Examples of heterocyclyl groups include oxazolidinyl, tetrahydrofuranyl, dihydrofuranyl, benzoxazinyl, benzthiazinyl, imidazolyl, benzimidazolyl, tetrazolyl, carbaxolyl, indolyl, phenoxazinyl, phenothiazinyl, dihydropyridinyl, dihydroisoxazolyl, dihydrobenzofuryl, azabicyclohexyl, thiazolidinyl, dihydroindolyl, pyridinyl, isoindole 1,3-dione, piperidinyl, tetrahydropyranyl, piperazinyl, 3H-imidazo[4,5-b]pyridine, isoquinolinyl, 1H-pyrrolo[2,3-b]pyridine or piperazinyl and the like.

"(Heteroaryl) alkyl" refers to alkyl-heteroaryl group linked through alkyl portion, wherein the alkyl and heteroaryl are as defined earlier.

"(Heterocyclyl) alkyl" refers to alkyl-heterocyclyl group linked through alkyl portion, wherein the alkyl and heterocyclyl are as defined earlier.

"Acyl" refers to —$C(=O)R_z$ wherein $R_z$ is same as defined earlier.

"Thiocarbonyl" refers to —C(=S)H. "Substituted thiocarbonyl" refers to —C(=S)R''', wherein R''' is selected from alkyl, cycloalkyl, aryl, aralkyl, heteroaryl, heterocyclyl, heteroarylalkyl, heterocyclylalkyl, amine or substituted amine. Unless otherwise constrained by the definition, all substituents optionally may be substituted further by 1-3 substituents selected from alkyl, aralkyl, cycloalkyl, aryl, heteroaryl, heterocyclyl, carboxy, hydroxy, alkoxy, halogen, $CF_3$, cyano, —C(=O)$NR_fR_q$, —O(C=O)$NR_fR_q$ (wherein $R_f$ and $R_q$ are the same as defined earlier), —(SO)$_nR_d$ (wherein n and $R_d$ are the same as defined earlier).

"Amine," unless otherwise specified, refers to —$NH_2$. "Substituted amino" unless otherwise specified, refers to a group —$N(R_k)_2$ wherein each $R_k$ is independently selected from the group hydrogen provided that both $R_k$ groups are not hydrogen (defined as "amino"), alkyl, alkenyl, alkynyl, aralkyl, cycloalkyl, aryl, heteroaryl, heterocyclyl, heterocyclylalkyl, heteroarylalkyl, acyl, S(O)$_mR_\psi$ (wherein m and $R_\psi$ are the same as defined above), —C(=$R_v$)$NR_\lambda R_y$ (wherein $R_v$ is O or S & $R_\lambda$ and $R_y$ are the same as defined earlier) or NHC(=$R_v$)$NR_yR_\lambda$ (wherein $R_v$, $R_y$ and $R_\lambda$ are the same as defined earlier). Unless otherwise constrained by the definition, all amino substituents may optionally be further substituted by 1-3 substituents chosen from alkyl, aralkyl, cycloalkyl, aryl, heteroaryl, heterocyclyl, carboxy, —COO$R_\psi$ (wherein $R_\psi$ is the same as defined earlier), hydroxy, alkoxy, halogen, $CF_3$, cyano, —C(=$R_v$)$NR_\lambda R_y$ (wherein $R_v$ is the same as defined earlier), —O(C=O)$NR_\lambda R_y$, —OC(=$R_v$)$NR_\lambda R_y$ (wherein $R_\lambda$, $R_y$ and $R_v$ are the same as defined earlier), —S(O)$_mR_\psi$ (wherein $R_\psi$ and m are the same as defined above).

The term "halogen" refers to fluorine, chlorine, bromine or iodine.

The compounds of the present invention can be used for treating CNS diseases, AIDS, asthma, arthritis, bronchitis, chronic obstructive pulmonary disease, psoriasis, allergic rhinitis, shock, atopic dermatitis, Crohn's disease, adult respiratory distress syndrome (ARDS), eosinophilic granuloma, allergic conjunctivitis, osteoarthritis, ulcerative colitis and other inflammatory diseases.

In accordance with yet another aspect, there are provided processes for the preparation of the compounds as described herein.

DETAILED DESCRIPTION OF THE INVENTION

The compounds described herein may be prepared by techniques well known in the art and familiar to the average synthetic organic chemist. In addition, the compounds of present invention may be prepared by the following, for example, reaction sequences as depicted in Scheme I.

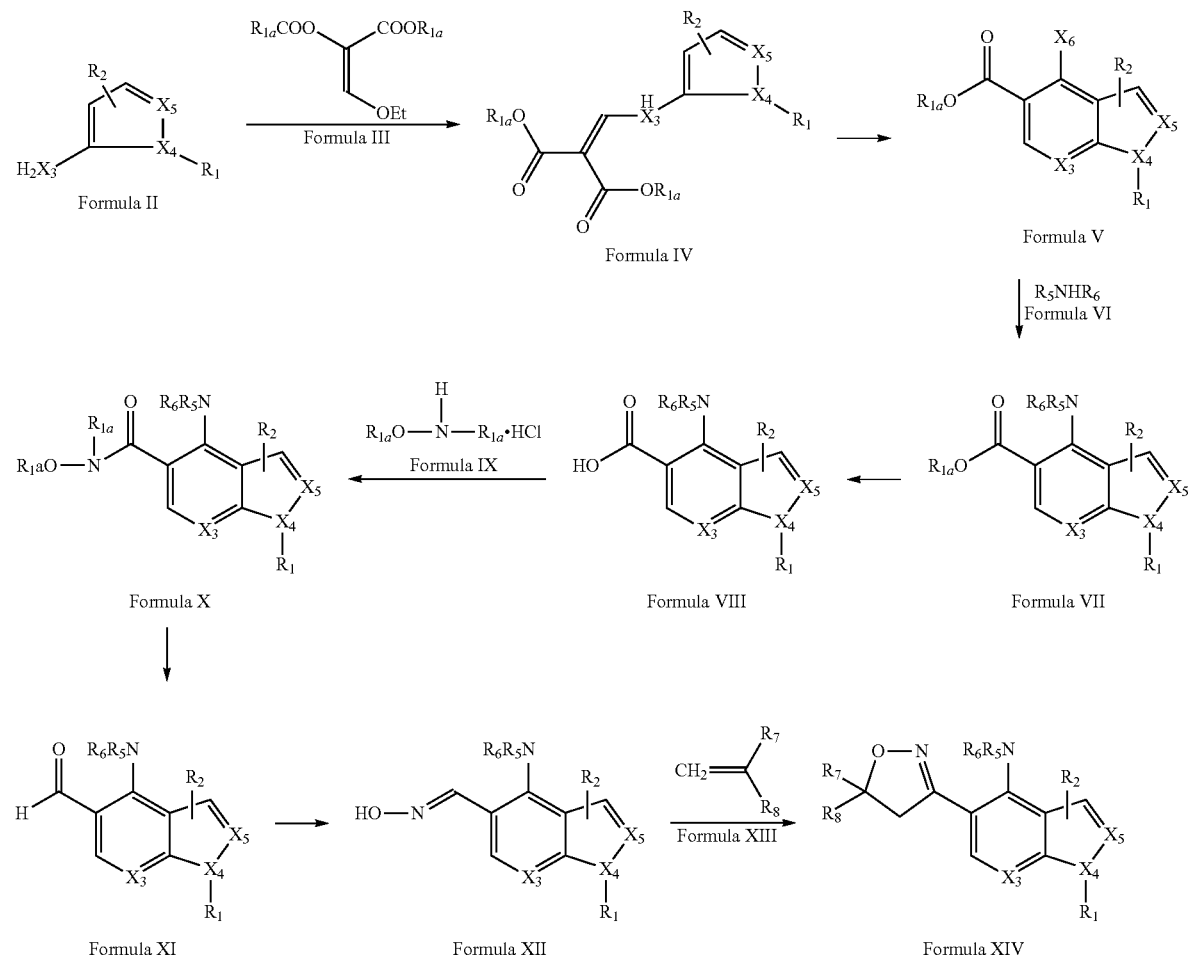

Scheme I

The compounds of Formula XIV can be prepared, for example, by following Scheme I. Thus, compounds of Formula II can be reacted with compounds of Formula III to give compounds of Formula IV (wherein $R_{1a}$ is alkyl), which on reaction with phosphorous oxy halide can give compounds of Formula V (wherein $X_6$ is a halogen), which on reaction with compounds of Formula VI can give compounds of Formula VII (wherein $R_5$ and $R_6$ are the same as defined earlier), which on ester hydrolysis can give compounds of Formula VIII, which on reaction with compounds of Formula IX can give compounds of Formula X, which on reduction can give compounds of Formula XI, which on reaction with hydroxylamine hydrochloride can give compounds of Formula XII, which can be finally reacted with compounds of Formula XIII to give compounds of Formula XIV (wherein $R_1$, $R_2$, $R_7$, $R_8$, $X_3$, $X_4$ and $X_5$ are the same as defined earlier).

The compounds of Formula IV can be prepared by the reaction of compounds of Formula II with compounds of Formula III with heating.

The compounds of Formula V can be prepared by the reaction of compounds of Formula IV with phosphorous oxy halide with heating.

The reaction of compounds of Formula V with compounds of Formula VI to give compounds of Formula VII can be carried out in one or more: nitrites, for example, acetonitrile; ketones, for example, acetone; alcohols, for example, ethanol; ethers, for example, tetrahydrofuran; amides, for example, dimethylformamide; sulfoxides, for example, dimethylsulfoxide; or hydrocarbons, for example, toluene.

The ester hydrolysis of compounds of Formula VII to give compounds of Formula VIII can be carried out in one or more alcohols, for example, methanol, ethanol or an alcohol and water mixture. The ester hydrolysis of compounds of Formula VII to give compounds of Formula VIII can be carried out in the presence of one or more inorganic bases, for example, potassium hydroxide, sodium hydroxide or lithium hydroxide.

The reaction of compounds of Formula VIII with compounds of Formula IX to give compounds of Formula X can be carried out in the presence of one or more activating reagents, for example, 1-hydroxybenzotriazole, acetone oxime or 2-hydroxypyridine, and one or more coupling reagents, for example, 1-(3-dimethylaminopropyl)-3-ethyl carbodiimide hydrochloride or 1,3-dicyclohexyl carbodiimide in one or more: ethers, for example, tetrahydrofuran; amides, for example, dimethylformamide; or sulfoxides, for example, dimethylsulfoxide. The reaction of compounds of Formula VIII with compounds of Formula IX can be carried out in the presence of one or more tertiary amine bases, for example, N-methylmorpholine, N-ethyldiisopropylamine or 4-dialkylaminopyridines.

The reduction of compounds of Formula X to give compounds of Formula XI can be carried out in one or more: ethers, for example, tetrahydrofuran; amides, for example, dimethylformamide; sulfoxides, for example, dimethylsulfoxide; or hydrocarbons, for example, toluene. The reduction of compounds of Formula X to give compounds of Formula XI can be carried out in the presence of one or more reducing agents, for example, sodium bis(2-methoxyethoxy)aluminum hydride or lithium aluminium hydride.

The reaction of compounds of Formula XI with hydroxylamine hydrochloride to give compounds of Formula XII can be carried out in the presence of sodium acetate in one or more alcohols, for example, methanol or ethanol.

The reaction of compounds of Formula XII with compounds of Formula XIII to give compounds of Formula XIV can be carried out in the presence of one or more halogenating agents, for example, sodium hypochlorite, N-chlorosuccinimide or N-bromosuccinimide in one or more: nitrites, for example, acetonitrile; ketones, for example, acetone; alcohols, for example, ethanol; ethers, for example, tetrahydrofuran; amides, for example, dimethylformamide; sulfoxides, for example, dimethylsulfoxide; or hydrocarbons, for example, toluene.

In the above schemes, where the specific solvents, bases, reducing agents, oxidizing agents, activating reagents, coupling reagents, halogenating agents etc., are mentioned, it is to be understood that other solvents, bases, reducing agents, oxidizing agents, activating reagents, coupling reagents, halogenating agents etc., known to those skilled in the art may be used. Similarly, reaction parameters such as the reaction temperature and duration may be adjusted according to the desired needs.

An illustrative list of compounds of the invention includes these listed below:

Methyl 3-[4-(cyclopropylamino)-1-ethyl-1H-pyrazolo[3,4-b]pyridin-5-yl]-5-methyl-4,5-dihydroisoxazole-5-carboxylate (Compound No. 1), {3-[4-(Cyclopropylamino)-1-ethyl-1H-pyrazolo[3,4-b]pyridin-5-yl]-5-methyl-4,5-dihydroisoxazol-5-yl}methanol (Compound No. 2), 3-[4-(Cyclopropylamino)-1-ethyl-1H-pyrazolo[3,4-b]pyridin-5-yl]-5-methyl-4,5-dihydroisoxazole-5-carbonitrile (Compound No. 3), Methyl 3-[4-(cyclopropylamino)-1-ethyl-1H-pyrazolo[3,4-b]pyridin-5-yl]-5-(2-methoxy-2-oxoethyl)-4,5-dihydroisoxazole-5-carboxylate (Compound No. 4), 5-(Carboxymethyl)-3-[4-(cyclopropylamino)-1-ethyl-1H-pyrazolo[3,4-b]pyridin-5-yl]-4,5-dihydroisoxazole-5-carboxylic acid (Compound No. 5), 5-(2-Amino-2-oxoethyl)-3-[4-(cyclopropylamino)-1-ethyl-1H-pyrazolo[3,4-b]pyridin-5-yl]-4,5-dihydroisoxazole-5-carboxamide (Compound No. 6), 2-[3-[4-(Cyclopropylamino)-1-ethyl-1H-pyrazolo[3,4-b]pyridin-5-yl]-5-(hydroxymethyl)-4,5-dihydroisoxazol-5-yl]ethanol (Compound No. 7), 3-[4-(Cyclopropylamino)-1-ethyl-1H-pyrazolo[3,4-b]pyridin-5-yl]-5-methyl-4,5-dihydroisoxazole-5-carboxamide (Compound No. 8), 3-[4-(Cyclopropylamino)-1-ethyl-1H-pyrazolo[3,4-b]pyridin-5-yl]-5-methyl-4,5-dihydroisoxazole-5-carboxylic acid (Compound No. 9), Methyl 3-[4-(cyclopentylamino)-1,3-dimethyl-1H-pyrazolo[3,4-b]pyridin-5-yl]-5-methyl-4,5-dihydroisoxazole-5-carboxylate (Compound No. 10), 3-[4-(Cyclopentylamino)-1,3-dimethyl-1H-pyrazolo[3,4-b]pyridin-5-yl]-N,5-dimethyl-4,5-dihydroisoxazole-5-carboxamide (Compound No. 11), 3-[4-(Cyclopentylamino)-1,3-dimethyl-1H-pyrazolo[3,4-b]pyridin-5-yl]-5-methyl-4,5-dihydroisoxazole-5-carboxamide (Compound No. 12), 5-(2-Amino-2-oxoethyl)-3-[4-(cyclopentylamino)-1,3-dimethyl-1H-pyrazolo[3,4-b]pyridin-5-yl]-4,5-dihydroisoxazole-5-carboxamide (Compound No. 13), Methyl 3-[4-(cyclopentylamino)-1,3-dimethyl-1H-pyrazolo[3,4-b]pyridin-5-yl]-5-(2-methoxy-2-oxoethyl)-4,5-dihydroisoxazole-5-carboxylate (Compound No. 14), {3-[4-(Cyclopentylamino)-1,3-dimethyl-1H-pyrazolo[3,4-b]pyridin-5-yl]-5-methyl-4,5-dihydroisoxazol-5-yl}methanol (Compound No. 15), Methyl 3-[4-(cyclopropylamino)-1,3-dimethyl-1H-pyrazolo[3,4-b]pyridin-5-yl]-5-(2-methoxy-2-oxoethyl)-4,5-dihydroisoxazole-5-carboxylate (Compound No. 16), Methyl 3-[4-(cyclopentylamino)-1-ethyl-1H-pyrazolo[3,4-b]pyridin-5-yl]-5-methyl-4,5-dihydroisoxazole-5-carboxylate (Compound No. 17), 2-[3-[4-(Cyclopentylamino)-1,3-dimethyl-1H-pyrazolo[3,4-b]pyridin-5-yl]-5-(hydroxymethyl)-4,5-dihydroisoxazol-5-yl]ethanol (Compound No. 18), Methyl 3-[4-(cyclopropylamino)-1,3-dimethyl-1H-pyrazolo[3,4-b]pyridin-5-yl]-5-methyl-4,5-dihydroisoxazole-5-carboxylate (Compound No. 19), {3-[4-(Cyclopropylamino)-1,3-dimethyl-1H-pyrazolo[3,4-b]pyridin-5-yl]-5-methyl-4,5-dihydroisoxazol-5-yl}methanol (Compound No. 20), N-cyclopropyl-3-[4-(cyclopropylamino)-1,3-dimethyl-1H-pyrazolo[3,4-b]pyridin-5-yl]-5-[2-(cyclopropylamino)-2-oxoethyl]-4,5-dihydroisoxazole-5-carboxamide (Compound No. 21), 5-(2-Amino-2-oxoethyl)-3-[4-(cyclopropylamino)-1,3-dimethyl-1H-pyrazolo[3,4-b]pyridin-5-yl]-4,5-dihydroisoxazole-5-carboxamide (Compound No. 22), Methyl 3-[4-(cyclopentylamino)-1-ethyl-1H-pyrazolo[3,4-b]pyridin-5-yl]-5-(2-methoxy-2-oxoethyl)-4,5-dihydroisoxazole-5-carboxylate (Compound No. 23), {3-[4-(Cyclopentylamino)-1-ethyl-1H-pyrazolo[3,4-b]pyridin-5-yl]-5-methyl-4,5-dihydroisoxazol-5-yl}methanol (Compound No. 24), and pharmaceutically acceptable salts, pharmaceutically acceptable solvates, stereoisomers, tautomers, racemates, regioisomers, prodrugs, metabolites, polymorphs or N-oxides, thereof.

The term "pharmaceutically acceptable" means approved by regulatory agency of the federal or a state government or listed in the U.S. Pharmacopoeia or other generally recognized pharmacopoeia for use in animals, and more particularly in humans.

The term "pharmaceutically acceptable salts" refers to derivatives of compounds that can be modified by forming their corresponding acid or base salts. Examples of pharmaceutically acceptable salts include, but are not limited to, mineral or organic acids salts of basic residues (such as amines), or alkali or organic salts of acidic residues (such as carboxylic acids), and the like.

The salt forms differ from the compound described herein in certain physical properties such as solubility, but the salts are otherwise equivalent for purposes of this invention.

The term "pharmaceutically acceptable solvates" refers to solvates with water (i.e. hydrates, hemihydrate or sesquihydrate) or pharmaceutically acceptable solvents, for example solvates with common organic solvents as ethanol and the like. Such solvates are also encompassed within the scope of the disclosure.

The present invention also includes within its scope prodrugs of these agents. In general, such prodrugs will be functional derivatives of these compounds, which are readily convertible in vivo into the required compound. Conventional procedures for the selection and preparation of prodrugs are known.

The disclosed compounds may get metabolized in vivo and these metabolites are also encompassed within the scope of this invention.

The term "polymorphs" includes all crystalline form as well as amorphous form for compounds described herein and are included in the present invention.

All stereoisomers of the compounds of the invention are contemplated, either in admixture or in pure or substantially pure form. The compounds of the present invention can have asymmetric centers at any of the carbon atoms including all the substituents. Consequently, compounds of present invention can exist in enantiomeric or diastereomeric forms or in mixture thereof. The processes for the preparation can utilize racemates, enantiomers, or diastereomers as starting materials. When diastereomeric or enantiomeric products are prepared, they can be separated by conventional methods, for example, chromatographic or fractional crystallization.

The term "tautomer" includes one of two or more structural isomers that exist in equilibrium and are readily converted from one isomeric form to another. Certain compounds of the general formula (I) may furthermore be present in tautomeric forms.

The term "regioisomers" refers to compounds, which have the same molecular formula but differ in the connectivity of the atoms.

The term "compounds of the invention", and equivalent expressions, are meant to embrace compounds of Formula (I) as herein described, including pharmaceutically acceptable salts, pharmaceutically acceptable solvates, stereoisomers, tautomers, racemates, regioisomers, prodrugs, metabolites, polymorphs or N-oxides, thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits.

The term "stable compound" means a compound that is sufficiently robust to survive isolation to a useful degree of purity from a reaction mixture, and formulation into an efficacious therapeutic or diagnostic agent. For example, a compound, which would have a "dangling valency" or is a "carbanion" is not a compound contemplated by the invention.

The term "racemate" includes a mixture of equal amounts of left- and right-handed stereoisomers of chiral molecules.

When a bond to a substituent is shown to cross a bond connecting two atoms in a ring, then such substituent may be bonded to any atom on the ring.

The present disclosure includes all isotopes of atoms occurring in the present compounds. Isotopes include those atoms having the same atomic number but different mass numbers. By way of general example, and without limitation, isotopes of hydrogen include tritium and deuterium. Isotopes of carbon include C-13 and C-14.

In another aspect, the present invention includes within its scope pharmaceutical compositions comprising, as an active ingredient, at least one of the disclosed compound or a pharmaceutically acceptable salt together with a pharmaceutically acceptable carrier or diluent. Compounds disclosed herein may be administered to human or animal for treatment by any route, which effectively transports the active compound to the appropriate or desired site of action such as oral, nasal, pulmonary, transdermal or parenteral (rectal, subcutaneous, intravenous, intraurethral, intramuscular, intranasal). The pharmaceutical composition of the present invention comprises a pharmaceutically effective amount of a compound of the present invention formulated together with one or more pharmaceutically acceptable carriers. The term "pharmaceutically acceptable carriers" is intended to include non-toxic, inert solid, semi-solid or liquid filler, diluents, encapsulating material or formulation of any type.

Where desired, the compounds of Formula I and/or their pharmaceutically acceptable salts, pharmaceutically acceptable solvates, stereoisomers, tautomers, racemates, regioisomers, prodrugs, metabolites, polymorphs or N-oxides may be advantageously used in combination with one or more other therapeutic agents. Examples of other therapeutic agents, which may be used in combination with compounds of Formula I of this invention and/or their pharmaceutically acceptable salts, pharmaceutically acceptable solvates, stereoisomers, tautomers, racemates, regioisomers, pro drugs, metabolites, polymorphs or N-oxides include corticosteroids, β2-agonists, leukotriene antagonists, 5-lipoxygenase inhibitors, chemokine inhibitors and muscarinic receptor antagonists.

The one or more β2-agonists may be chosen from those in the art or subsequently discovered. The β2-agonists may include one or more compounds described in U.S. Pat. Nos. 3,705,233; 3,644,353; 3,642,896; 3,700,681; 4,579,985; 3,994,974; 3,937,838; 4,419,364; 5,126,375; 5,243,076; 4,992,474; and 4,011,258.

Suitable β2-agonists include, for example, one or more of albuterol, salbutamol, biltolterol, pirbuterol, levosalbutamol, tulobuterol, terbutaline, bambuterol, metaproterenol, fenoterol, salmeterol, carmoterol, arformoterol, formoterol, and their pharmaceutically acceptable salts or solvates thereof.

Corticosteroids as described herein may be chosen from those in the art or subsequently discovered. Suitable corticosteroids may be include one or more compounds described in U.S. Pat. Nos. 3,312,590; 3,983,233; 3,929,768; 3,721,687; 3,436,389; 3,506,694; 3,639,434; 3,992,534; 3,928,326; 3,980,778; 3,780,177; 3,652,554; 3,947,478; 4,076,708; 4,124,707; 4,158,055; 4,298,604; 4,335,121; 4,081,541; 4,226,862; 4,290,962; 4,587,236; 4,472,392; 4,472,393; 4,242,334; 4,014,909; 4,098,803; 4,619,921; 5,482,934; 5,837,699; 5,889,015; 5,278,156; 5,015,746; 5,976,573; 6,337,324; 6,057,307; 6,723,713; 6,127,353; and 6,180,781.

Suitable corticosteroids may include, for example, one or more of aldlometasone, amcinonide, amelometasone, beclometasone, betamethasone, budesonide, ciclesonide, clobetasol, cloticasone, cyclomethasone, deflazacort, deprodone, dexbudesonide, diflorasone, difluprednate, fluticasone, flunisolide, halometasone, halopredone, hydrocortisone, hydrocortisone, methylprednisolone, mometasone, prednicarbate, prednisolone, rimexolone, tixocortol, triamcinolone, tolterodine, oxybutynin, ulobetasol, rofleponide, GW 215864, KSR 592, ST-126, dexamethasone and pharmaceutically acceptable salts, solvates thereof. Preferred corticosteroids include, for example, flunisolide, beclomethasone, triamcinolone, budesonide, fluticasone, mometasone, ciclesonide, and dexamethasone, while budesonide, fluticasone, mometasone, ciclesonide. Examples of possible salts or derivatives include: sodium salts, sulfobenzoates, phosphates, isonicotinates, acetates, propionates, dihydrogen phosphates, palmitates, pivalates, or furoates. In some cases, the corticosteroids may also occur in the form of their hydrates.

Suitable muscarinic receptor antagonists include substances that directly or indirectly block activation of muscarinic cholinergic receptors. Examples include, but are not limited to, quaternary amines (e.g., methantheline, ipratropium, propantheline), tertiary amines (e.g., dicyclomine, scopolamine) and tricyclic amines (e.g., telenzepine). Other suitable muscarinic receptor antagonists include benztropine (commercially available as COGENTIN® from Merck), hexahydro-sila-difenidol hydrochloride (HHSID hydrochloride disclosed in Lambrecht et al., *Trends in Pharmacol. Sci.,* 10(Suppl):60 (1989); (+/−)-3-quinuclidinyl xanthene-9-carboxylate hemioxalate (QNX-hemioxalate; Birdsall et al., *Trends in Pharmacol. Sci.,* 4:459 (1983); telenzepine dihydrochloride (Coruzzi et al., *Arch. Int. Pharmacodyn. Ther.,* 302:232 (1989); and Kawashima et al., *Gen. Pharmacol,* 21:17 (1990)), and atropine.

The leukotriene antagonist can be selected from compounds, for example, those described in U.S. Pat. No. 5,565, 473, U.S. Pat. No. 5,583,152, U.S. Pat. No. 4,859,692 or U.S. Pat. No. 4,780,469.

Examples of leukotriene antagonist include, but are not limited to, montelukast, zafirlukast, pranlukast and pharmaceutically acceptable salts thereof.

5-Lipoxygenase inhibitors can be selected from for example, compounds in U.S. Pat. No. 4,826,868, or 4,873, 259, or European Patent Nos. EP 419049, EP 542356 or EP 542355. Examples may include, but are not limited to, atreleuton, zyflo (zileuton), ABT-761, fenleuton or tepoxalin.

Examples of the chemokine inhibitors include, but are not limited to, endogenous ligands of chemokine receptors or derivatives thereof, and non-peptidic low molecular compounds or antibodies for chemokine receptors.

Examples of the endogenous ligands of chemokine receptors include, but are not limited to, MIP-1α, MIP-1β, Rantes, SDF-1α, SDF-1β, MCP-1, MCP-2, MCP4, Eotaxin, MDC. Examples of the derivatives of endogenous ligands include, but are not limited to, AOP-RANTES, Met-SDF-1α, Met-SDF-1β.

Examples of the antibodies for chemokine receptors include, but are not limited to, Pro-140.

Examples of the non-peptidic low molecular compounds include, but are not limited to, antagonists and agonists for CCR1, CCR2, CCR3, CCR4, CCR5, CXCR1, CXCR2, CXCR3 and CXCR4 receptors.

Examples set forth below demonstrate the synthetic procedures for the preparation of the representative compounds. The examples are provided to illustrate particular aspect of the disclosure and do not constrain the scope of the present invention as defined by the claims.

EXPERIMENTAL DETAILS

Example 1

Preparation of Diethyl {[(1-ethyl-1H-pyrazol-5-yl)amino]methylene}malonate

A mixture of 5-amino-1-ethylpyrazole (1 gm, 0.0089 mole) and diethylethoxymethylenemalonate (1.9 ml, 0.0089 mole) was stirred at 120° C. for about 1 hour. The reaction mixture was poured into water and extraction was done with ethyl acetate. The organic layer was dried over anhydrous sodium sulfate and concentrated in vacuo to give yellow oil. Yield: 2.5 g. m/z: (M$^+$+1) 282.0.

The following compound was prepared similarly
Diethyl {[(1,3-dimethyl-1H-pyrazol-5-yl)amino]methylene}malonate Example 2

Preparation of ethyl-4-chloro-1-ethyl-1H-pyrazolo[3,4-b]pyridine-5-carboxylate

A mixture of diethyl {[(1-ethyl-1H-pyrazol-5-yl)amino]methylene}malonate (2.5 g, 0.009 mole) and phosphorous oxy chloride (17.7 ml, 0.185 mole) was heated at 110-120° C. under stirring for about 3 hours under argon atmosphere. The reaction mixture was poured into ice water. It was extracted with dichloromethane and washed with brine. The organic layer was dried over anhydrous sodium sulfate and concentrated in vacuo to give pure white solid compound. Yield: 1.8 g. m/z: (M$^+$+1) 253.9.

The following compound was prepared similarly.
Ethyl-4-chloro-1,3-dimethyl-1H-pyrazolo[3,4-b]pyridine-5-carboxylate

Example 3

Preparation of ethyl-4-cyclopropylamino-1-ethyl-1H-pyrazolo[3,4-b]pyridine-5-carboxylate To a mixture of ethyl 4-chloro-1-ethyl-1H-pyrazolo[3,4-b]pyridine-5-carboxylate (950 mg, 0.0037 mole) in acetonitrile, cyclopropyl amine (0.525 ml, 0.0074 mole) was added. After stirring for about 2 hours at 110° C., acetonitrile was removed under reduced pressure. Water was added and the reaction mixture was extracted with ethyl acetate. The organic layer was washed with brine, dried over anhydrous sodium sulfate and concentrated in vacuo to give light yellow solid compound. Yield: 1 g. m/z: (M$^+$+1) 275.0.

The following compounds were prepared similarly
Ethyl 4-(cyclopropylamino)-1,3-dimethyl-1H-pyrazolo[3,4-b]pyridine-5-carboxylate
Ethyl 4-(cyclopentylamino)-1-ethyl-1H-pyrazolo[3,4-b]pyridine-5-carboxylate
Ethyl 4-(cyclopentylamino)-1,3-dimethyl-1H-pyrazolo[3,4-b]pyridine-5-carboxylate

Example 4

Preparation of 4-cyclopropylamino-1-ethyl-1H-pyrazolo[3,4-b]pyridine-5-carboxylic acid To a solution of ethyl 4-cyclopropylamino-1-ethyl-1H-pyrazolo[3,4-b]pyridine-5-carboxylate (1 g, 0.0036 mole) in ethanol, sodium hydroxide solution (440 mg in 2 ml water) was added. The reaction mixture was stirred for about 14 hours at ambient temperature. Water was added and the reaction mixture was extracted with ethyl acetate. Aqueous layer was acidified by using hydrochloric acid (2N) to pH of about 4-5. White solid, which was obtained, was filtered and dried in vacuo.
Yield: 560 mg. m/z: (M$^+$+1) 274.2.
The following compounds were prepared similarly.
4-(Cyclopropylamino)-1,3-dimethyl-1H-pyrazolo[3,4-b]pyridine-5-carboxylic acid
4-(Cyclopentylamino)-1-ethyl-1H-pyrazolo[3,4-b]pyridine-5-carboxylic acid
4-(Cyclopentylamino)-1,3-dimethyl-1H-pyrazolo[3,4-b]pyridine-5-carboxylic acid

Example 5

Preparation of 4-(cyclo-propylamino)-1-ethyl-N-methoxy-N-methyl-1H-pyrazolo[3,4-b]pyridine-5-carboxamide 4-cyclopropylamino-1-ethyl-1H-pyrazolo[3,4-b]pyridine-5-carboxylic acid (500 mg, 0.0020 mole) and N,O-dimethylhydroxylamine hydrochloride (298 mg, 0.0030 mole) were taken in dimethylformamide. At 0° C., hydroxybenzotriazole (550 mg, 0.0040 mole) and N-methylmorpholine (1.34 ml, 0.012 mole) were added and the reaction mixture was stirred for about 1 hour. 1-(3-dimethylaminopropyl) 3-ethyl carbodiimide hydrochloride (780 mg, 0.0040 mole) was added and the reaction mixture was stirred for about 14 hours. Water was added and extraction was carried out with ethyl acetate. The organic layer was washed with brine, dried over anhydrous sodium sulfate and concentrated in vacuo to give an oily compound. Yield: 500 mg. m/z: (M$^+$+1) 290.2.
The following compounds were prepared similarly
4-(Cyclopropylamino)-N-methoxy-N-1,3-trimethyl-1H-pyrazolo[3,4-b]pyridine-5-carboxamide
4-(Cyclopentylamino)-1-ethyl-N-methoxy-N-methyl-1H-pyrazolo[3,4-b]pyridine-5-carboxamide
4-(Cyclopentylamino)-N-methoxy-N-1,3-trimethyl-1H-pyrazolo[3,4-b]pyridine-5-carboxamide

Example 6

Preparation of 4-cyclopropylamino-1-ethyl-1H-pyrazolo[3,4-b]pyridine-5-carbaldehyde Toluene was cooled at −19 to −20° C. and vitride (0.50 ml, 0.0034 mole) was added. After about 10 minutes, 4-(cyclopropylamino)-1-ethyl-N-methoxy-N-methyl-1H-pyrazolo[3,4-b]pyridine-5-carboxamide (500 mg, 0.0017 mole) was added and the reaction mixture was stirred for about 4 hours. Citric acid (10%) solution was added dropwise to quench the reaction and the reaction mixture was extracted with ethyl acetate. The organic layer was washed with brine and dried over anhydrous sodium sulfate and concentrated in vacuo to give an oily compound. Yield: 300 mg. m/z: (M$^+$+1) 231.1.
The following compounds were prepared similarly.
4-(Cyclopropylamino)-1,3-dimethyl-1H-pyrazolo[3,4-b]pyridine-5-carbaldehyde
4-(Cyclopentylamino)-1-ethyl-1H-pyrazolo[3,4-b]pyridine-5-carbaldehyde
4-(Cyclopentylamino)-1,3-dimethyl-1H-pyrazolo[3,4-b]pyridine-5-carbaldehyde

Example 7

Preparation of 4-cyclopropylamino-1-ethyl-1H-pyrazolo[3,4-b]pyridine-5-carbaldehyde oxime To a stirred solution of 4-cyclopropylamino-1-ethyl-1H-pyrazolo[3,4-b]pyridine-5-carbaldehyde (300 mg, 0.00129 mole) in ethanol, hydroxylamine hydrochloride (359 mg, 0.0051 mole) and sodium acetate (424 mg, 0.0051 mole) were added. The reaction mixture was allowed to stir at room temperature for about 50 minutes. Ethanol was removed under reduced pressure and residue was poured in water. The organic compound was extracted with ethyl acetate. Ethyl acetate layer was dried over anhydrous sodium sulfate, filtered and finally concentrated under reduced pressure to afford white solid compound. Yield: 270 mg. m/z: (M$^+$+1) 246.1.
The following compounds were prepared similarly.
4-(Cyclopropylamino)-1,3-dimethyl-1H-pyrazolo[3,4-b]pyridine-5-carbaldehyde oxime
4-(Cyclopentylamino)-1-ethyl-1H-pyrazolo[3,4-b]pyridine-5-carbaldehyde oxime
4-(Cyclopentylamino)-1,3-dimethyl-1H-pyrazolo[3,4-b]pyridine-5-carbaldehyde oxime

Example 8

Preparation of methyl 3-[4-(cyclopropylamino)-1-ethyl-1H-pyrazolo[3,4-b]pyridin-5-yl]-5-methyl-4,5-dihydroisoxazole-5-carboxylate (Compound No. 1)

Methyl methacrylate (0.3 ml, 0.0028 mole) was added to 4-cyclopropylamino-1-ethyl-1H-pyrazolo[3,4-b]pyridine-5- carbaldehyde oxime (70 mg, 0.00028 mol) in tetrahydrofuran. The reaction mixture was stirred at room temperature. Sodium hypochlorite (2 ml) was added slowly to the mixture thus obtained over a period of about 5 minutes and the reaction mixture was allowed to stir at room temperature for about 4 hours. Tetrahydrofuran was evaporated and the organic layer was extracted with ethyl acetate. It was concentrated and purified by column chromatography to yield the title compound. Yield: 50 mg (51%). m/z: (M$^+$+1) 344.1.

The following compounds were prepared similarly

{3-[4-(Cyclopropylamino)-1-ethyl-1H-pyrazolo[3,4-b]pyridin-5-yl]-5-methyl-4,5-dihydroisoxazol-5-yl}methanol (Compound No. 2), Yield: (26.4%). m/z: (M$^+$+1) 316.2.

3-[4-(Cyclopropylamino)-1-ethyl-1H-pyrazolo[3,4-b]pyridin-5-yl]-5-methyl-4,5-dihydroisoxazole-5-carbonitrile (Compound No. 3), Yield: (26%). m/z: (M$^+$+1) 311.2.

Methyl 3-[4-(cyclopropylamino)-1-ethyl-1H-pyrazolo[3,4-b]pyridin-5-yl]-5-(2-methoxy-2-oxoethyl)-4,5-dihydroisoxazole-5-carboxylate (Compound No. 4), Yield: (83%). m/z: (M$^+$+1) 402.2.

5-(Carboxymethyl)-3-[4-(cyclopropylamino)-1-ethyl-1H-pyrazolo[3,4-b]pyridin-5-yl]-4,5-dihydroisoxazole-5-carboxylic acid (Compound No. 5), Yield: (45%). m/z: (M$^+$+1) 374.2.

5-(2-Amino-2-oxoethyl)-3-[4-(cyclopropylamino)-1-ethyl-1H-pyrazolo[3,4-b]pyridin-5-yl]-4,5-dihydroisoxazole-5-carboxamide (Compound No. 6), Yield: (86%). m/z: (M$^+$+1) 372.2.

2-[3-[4-(Cyclopropylamino)-1-ethyl-1H-pyrazolo[3,4-b]pyridin-5-yl]-5-(hydroxymethyl)-4,5-dihydroisoxazol-5-yl]ethanol (Compound No. 7), Yield: (83.4%). m/z: (M$^+$+1) 346.3.

3-[4-(Cyclopropylamino)-1-ethyl-1H-pyrazolo[3,4-b]pyridin-5-yl]-5-methyl-4,5-dihydroisoxazole-5-carboxamide (Compound No. 8), Yield: (83.6%). m/z: (M$^+$+1) 329.1.

3-[4-(Cyclopropylamino)-1-ethyl-1H-pyrazolo[3,4-b]pyridin-5-yl]-5-methyl-4,5-dihydroisoxazole-5-carboxylic acid (Compound No. 9), Yield: (62.5%). m/z: (M$^+$+1) 330.0.

Methyl 3-[4-(cyclopentylamino)-1,3-dimethyl-1H-pyrazolo[3,4-b]pyridin-5-yl]-5-methyl-4,5-dihydroisoxazole-5-carboxylate (Compound No. 10), Yield: (61.4%). m/z: (M$^+$+1) 372.1.

3-[4-(Cyclopentylamino)-1,3-dimethyl-1H-pyrazolo[3,4-b]pyridin-5-yl]-N, 5-dimethyl-4,5-dihydroisoxazole-5-carboxamide (Compound No. 11), Yield: (57.2%). m/z: (M$^+$+1) 371.1.

3-[4-(Cyclopentylamino)-1,3-dimethyl-1H-pyrazolo[3,4-b]pyridin-5-yl]-5-methyl-4,5-dihydroisoxazole-5-carboxamide (Compound No. 12), Yield: (44.5%). m/z: (M$^+$+1) 357.1.

5-(2-Amino-2-oxoethyl)-3-[4-(cyclopentylamino)-1,3-dimethyl-1H-pyrazolo[3,4-b]pyridin-5-yl]-4,5-dihydroisoxazole-5-carboxamide (Compound No. 13), Yield: (85.8%). m/z: (M$^+$+1) 400.1.

Methyl 3-[4-(cyclopentylamino)-1,3-dimethyl-1H-pyrazolo[3,4-b]pyridin-5-yl]-5-(2-methoxy-2-oxoethyl)-4,5-dihydroisoxazole-5-carboxylate (Compound No. 14), Yield: (60%). m/z: (M$^+$+1) 430.0.

{3-[4-(Cyclopentylamino)-1,3-dimethyl-1H-pyrazolo[3,4-b]pyridin-5-yl]-5-methyl-4,5-dihydroisoxazol-5-yl}methanol (Compound No. 15), Yield: (25.2%). m/z: (M$^+$+1) 344.1.

Methyl 3-[4-(cyclopropylamino)-1,3-dimethyl-1H-pyrazolo[3,4-b]pyridin-5-yl]-5-(2-methoxy-2-oxoethyl)-4,5-dihydroisoxazole-5-carboxylate (Compound No. 16), Yield: (30.6%). m/z: (M$^+$+1) 402.0.

Methyl 3-[4-(cyclopentylamino)-1-ethyl-1H-pyrazolo[3,4-b]pyridin-5-yl]-5-methyl-4,5-dihydroisoxazole-5-carboxylate (Compound No. 17), Yield: (42%). m/z: (M$^+$+1) 372.1.

2-[3-[4-(Cyclopentylamino)-1,3-dimethyl-1H-pyrazolo[3,4-b]pyridin-5-yl]-5-(hydroxymethyl)-4,5-dihydroisoxazol-5-yl]ethanol (Compound No. 18), Yield: (90%). m/z: (M$^+$+1) 374.2.

Methyl 3-[4-(cyclopropylamino)-1,3-dimethyl-1H-pyrazolo[3,4-b]pyridin-5-yl]-5-methyl-4,5-dihydroisoxazole-5-carboxylate (Compound No. 19), Yield: (15.3%). m/z: (M$^+$+1) 344.0.

{3-[4-(Cyclopropylamino)-1,3-dimethyl-1H-pyrazolo[3,4-b]pyridin-5-yl]-5-methyl-4,5-dihydroisoxazol-5-yl}methanol (Compound No. 20), Yield: (15.62%). m/z: (M$^+$+1) 316.1.

N-cyclopropyl-3-[4-(cyclopropylamino)-1,3-dimethyl-1H-pyrazolo[3,4-b]pyridin-5-yl]-5-[2-(cyclopropylamino)-2-oxoethyl]-4,5-dihydroisoxazole-5-carboxamide (Compound No. 21), Yield: (63.82%). m/z: (M$^+$+1) 474.1.

5-(2-Amino-2-oxoethyl)-3-[4-(cyclopropylamino)-1,3-dimethyl-1H-pyrazolo[3,4-b]pyridin-5-yl]-4,5-dihydroisoxazole-5-carboxamide (Compound No. 22), Yield: (86.2%). m/z: (M$^+$+1) 372.0.

Methyl 3-[4-(cyclopentylamino)-1-ethyl-1H-pyrazolo[3,4-b]pyridin-5-yl]-5-(2-methoxy-2-oxoethyl)-4,5-dihydroisoxazole-5-carboxylate (Compound No. 23), Yield: (51%). m/z: (M$^+$+1) 430.1.

{3-[4-(Cyclopentylamino)-1-ethyl-1H-pyrazolo[3,4-b]pyridin-5-yl]-5-methyl-4,5-dihydroisoxazol-5-yl}methanol (Compound No. 24), Yield: (63.9%). m/z: (M$^+$+1) 344.2.

Example 9

Efficacy of Compounds as PDE IV Inhibitors

PDE-IV Enzyme Assay

The efficacy of compounds of PDE-4 inhibitors was determined by an enzyme assay using U937 cell cytosolic fraction (*Biochem. Biophys. Res. Comm.*, 197: 1126-1131, 1993). The enzyme reaction was carried out in the presence of cAMP (1 μM) at 30° C. in the presence or absence of test compound for 45-60 min. An aliquot of this reaction mixture was taken further for the ELISA assay and the protocol of the kit was followed to determine level of cAMP in the sample. The concentration of the cAMP in the sample directly correlated with the degree of PDE-4 enzyme inhibition. Results were expressed as percent control and the IC$_{50}$ values of test compounds were found to be in the range of lower μM to nM concentration.

The PDE-IV inhibitor IC$_{50}$ values of the compounds specifically disclosed herein ranged from about 0.1 nM to about 10 μM, for example from about 0.1 nM to about 1.8 μM, or from about 0.1 nM to about 400 nM, or from about 0.1 nM to about 100 nM, for example from about 0.1 nM to about 50 mM, or from about 0.1 nM to about 10 nM.

We claim:

1. Compounds having the structure of Formula I:

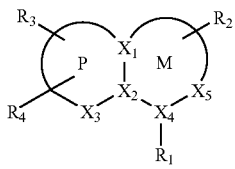

Formula I and their pharmaceutically acceptable salts, stereoisomers, tautomers, racemates, regioisomers or N-oxides, wherein ring P including $X_1$, $X_2$ and $X_3$ is a six-membered ring containing 1-3 double bonds wherein $X_1$ and $X_2$ are carbon and $X_3$ is nitrogen;

ring M (including $X_1$, $X_2$, $X_4$ and $X_5$) is a five-membered ring containing 1-2 double bonds, wherein $X_1$ and $X_2$ are carbon and $X_4$ and $X_5$ are nitrogen;

$R_1$ is hydrogen, alkyl, alkenyl, alkynyl, cycloalkyl, aryl, aralkyl, aralkenyl, (cycloalkyl) alkyl, heterocyclyl, heteroaryl, (heterocyclyl) alkyl or (heteroaryl) alkyl;

$R_2$ is hydrogen, alkyl, halogen, cyano, nitro, —SR, NRR, —$(CH_2)_n$OR {wherein R is hydrogen, alkyl, alkenyl, alkynyl, cycloalkyl, aryl, heteroaryl or heterocyclyl and n is an integer from 0-2}, alkenyl, alkynyl, cycloalkyl, (cycloalkyl) alkyl, aryl, aralkyl, aralkenyl, heterocyclyl, heteroaryl, (heterocyclyl) alkyl or (heteroaryl) alkyl;

$R_3$ is —$NR_5R_6$ {wherein $R_5$ and $R_6$ independently are hydrogen, alkyl, alkenyl, alkynyl, acyl, cycloalkyl, aryl, aralkenyl, aralkyl, (cycloalkyl) alkyl, heterocyclyl, heteroaryl, (heterocyclyl) alkyl or (heteroaryl) alkyl}; and $R_4$ is a radical of Formula I a or I b

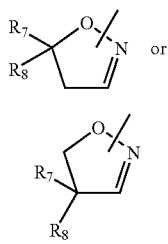

Formula Ia or

Formula Ib wherein $R_7$ and $R_8$ independently are alkyl, —CN, —$(CH_2)_n$C(=O)$NR_fR_q$ {wherein n is an integer from 0-2 and $R_f$ and $R_q$ independently are hydrogen, alkyl, alkenyl, cycloalkyl, aryl, aralkyl, heterocyclyl, heteroaryl, (heterocyclyl)alkyl, or (heteroaryl)alkyl}, —$(CH_2)_n$C(=O)$OR_f$ {wherein n and $R_f$ are the same as defined earlier}, or —$(CH_2)_n$OR_f$ {wherein n and $R_f$ are the same as defined earlier}.

2. A compound selected from:
Methyl 3-[4-(cyclopropylamino)-1-ethyl-1H-pyrazolo[3,4-b]pyridin-5-yl]-5-methyl-4,5-dihydroisoxazole-5-carboxylate,
{3-[4-(Cyclopropylamino)-1-ethyl-1H-pyrazolo[3,4-b]pyridin-5-yl]-5-methyl-4,5-dihydroisoxazol-5-yl}methanol,
3-[4-(Cyclopropylamino)-1-ethyl-1H-pyrazolo[3,4-b]pyridin-5-yl]-5-methyl-4,5-dihydroisoxazole-5-carbonitrile,
Methyl 3-[4-(cyclopropylamino)-1-ethyl-1H-pyrazolo[3,4-b]pyridin-5-yl]-5-(2-methoxy-2-oxoethyl)-4,5-dihydroisoxazole-5-carboxylate,
5-(Carboxymethyl)-3-[4-(cyclopropylamino)-1-ethyl-1H-pyrazolo[3,4-b]pyridin-5-yl]-4,5-dihydroisoxazole-5-carboxylic acid,
5-(2-Amino-2-oxoethyl)-3-[4-(cyclopropylamino)-1-ethyl-1H-pyrazolo[3,4-b]pyridin-5-yl]-4,5-dihydroisoxazole-5-carboxamide,
2-[3-[4-(Cyclopropylamino)-1-ethyl-1H-pyrazolo[3,4-b]pyridin-5-yl]-5-(hydroxymethyl)-4,5-dihydroisoxazol-5-yl]ethanol,
3-[4-(Cyclopropylamino)-1-ethyl-1H-pyrazolo[3,4-b]pyridin-5-yl]-5-methyl-4,5-dihydroisoxazole-5-carboxamide,
3-[4-(Cyclopropylamino)-1-ethyl-1H-pyrazolo[3,4-b]pyridin-5-yl]-5-methyl-4,5-dihydroisoxazole-5-carboxylic acid,
Methyl 3-[4-(cyclopentylamino)-1,3-dimethyl-1H-pyrazolo[3,4-b]pyridin-5-yl]-5-methyl-4,5-dihydroisoxazole-5-carboxylate,
3-[4-(Cyclopentylamino)-1,3-dimethyl-1H-pyrazolo[3,4-b]pyridin-5-yl]-N,5-dimethyl-4,5-dihydroisoxazole-5-carboxamide,
3-[4-(Cyclopentylamino)-1,3-dimethyl-1H-pyrazolo[3,4-b]pyridin-5-yl]-5-methyl-4,5-dihydroisoxazole-5-carboxamide,
5-(2-Amino-2-oxoethyl)-3-[4-(cyclopentylamino)-1,3-dimethyl-1H-pyrazolo[3,4-b]pyridin-5-yl]-4,5-dihydroisoxazole-5-carboxamide,
Methyl 3-[4-(cyclopentylamino)-1,3-dimethyl-1H-pyrazolo[3,4-b]pyridin-5-yl]-5-(2-methoxy-2-oxoethyl)-4,5-dihydroisoxazole-5-carboxylate,
{3-[4-(Cyclopentylamino)-1,3-dimethyl-1H-pyrazolo[3,4-b]pyridin-5-yl]-5-methyl-4,5-dihydroisoxazol-5-yl}methanol,
Methyl 3-[4-(cyclopropylamino)-1,3-dimethyl-1H-pyrazolo[3,4-b]pyridin-5-yl]-5-(2-methoxy-2-oxoethyl)-4,5-dihydroisoxazole-5-carboxylate,
Methyl 3-[4-(cyclopentylamino)-1-ethyl-1H-pyrazolo[3,4-b]pyridin-5-yl]-5-methyl-4,5-dihydroisoxazole-5-carboxylate,
2-[3-[4-(Cyclopentylamino)-1,3-dimethyl-1H-pyrazolo[3,4-b]pyridin-5-yl]-5-(hydroxymethyl)-4,5-dihydroisoxazol-5-yl]ethanol,
Methyl 3-[4-(cyclopropylamino)-1,3-dimethyl-1H-pyrazolo[3,4-b]pyridin-5-yl]-5-methyl-4,5-dihydroisoxazole-5-carboxylate,
{3-[4-(Cyclopropylamino)-1,3-dimethyl-1H-pyrazolo[3,4-b]pyridin-5-yl]-5-methyl-4,5-dihydroisoxazol-5-yl}methanol,
N-cyclopropyl-3-[4-(cyclopropylamino)-1,3-dimethyl-1H-pyrazolo[3,4-b]pyridin-5-yl]-5-[2-(cyclopropylamino)-2-oxoethyl]-4,5-dihydroisoxazole-5-carboxamide,
5-(2-Amino-2-oxoethyl)-3-[4-(cyclopropylamino)-1,3-dimethyl-1H-pyrazolo[3,4-b]pyridin-5-yl]-4,5-dihydroisoxazole-5-carboxamide,
Methyl 3-[4-(cyclopentylamino)-1-ethyl-1H-pyrazolo[3,4-b]pyridin-5-yl]-5-(2-methoxy-2-oxoethyl)-4,5-dihydroisoxazole-5-carboxylate, or
{3-[4-(Cyclopentylamino)-1-ethyl-1H-pyrazolo[3,4-b]pyridin-5-yl]-5-methyl-4,5-dihydroisoxazol-5-yl}methanol,
and their pharmaceutically acceptable salts, stereoisomers, tautomers, racemates, regioisomers or N-oxides.

3. Pharmaceutical compositions comprising a therapeutically effective amount of a compound of claim 1, together with at least one pharmaceutically acceptable carrier, excipient or diluent.

4. Pharmaceutical compositions comprising a therapeutically effective amount of a compound of claim 1 and at least one other active ingredient selected from corticosteroids, β2-agonists, leukotriene antagonists, 5-lipoxygenase inhibitors, chemokine inhibitors and muscarinic receptor antagonists.

5. A method for the preparation of compounds of Formula XIV,

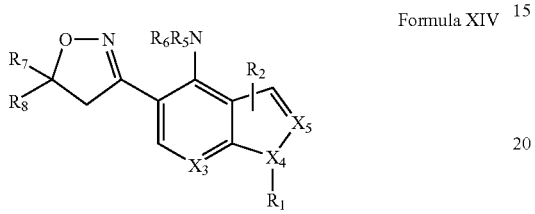

Formula XIV and their pharmaceutically acceptable salts, stereoisomers, tautomers, racemates, regioisomers or N-oxides, wherein $R_1$, $R_2$, $R_5$, $R_6$, $R_7$, $R_8$, are $X_3$, $X_4$ and $X_5$ are nitrogen;

$R_1$ is hydrogen, alkyl, alkenyl, alkynyl, cycloalkyl, aryl, aralkyl, aralkenyl, (cycloalkyl) alkyl, heterocyclyl, heteroaryl, (heterocyclyl) alkyl or (heteroaryl) alkyl;

$R_2$ is hydrogen, alkyl, halogen, cyano, nitro, —SR, NRR, —(CH$_2$)$_n$OR {wherein R is hydrogen, alkyl, alkenyl, alkynyl, cycloalkyl, aryl, heteroaryl or heterocyclyl and n is an integer from 0-2}, alkenyl, alkynyl, cycloalkyl, (cycloalkyl) alkyl, aryl, aralkyl, aralkenyl, heterocyclyl, heteroaryl, (heterocyclyl) alkyl or (heteroaryl) alkyl;

$R_5$ and $R_6$ independently are hydrogen, alkyl, alkenyl, alkynyl, acyl, cycloalkyl, aryl, aralkenyl, aralkyl, (cycloalkyl) alkyl, heterocyclyl, heteroaryl, (heterocyclyl) alkyl or (heteroaryl) alkyl; and $R_7$ and $R_8$ independently are alkyl, —CN, —(CH$_2$)$_n$C(=O)NR$_f$R$_q$ {wherein n is an integer from 0-2 and R$_f$ and R$_q$ independently are hydrogen, alkyl, alkenyl, cycloalkyl, aryl, aralkyl, heterocyclyl, heteroaryl, (heterocyclyl)alkyl, or (heteroaryl)alkyl}, —(CH$_2$)$_n$C(=O)OR$_f$ {wherein n and R$_f$ are the same as defined earlier}, or —(CH$_2$)$_n$OR$_f$ {wherein n and R$_f$ are the same as defined earlier}, the method comprising (a) reacting a compound of Formula II with a compound of Formula III to give a compound of Formula IV (wherein $R_{1a}$ is alkyl);

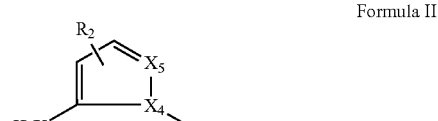

Formula II

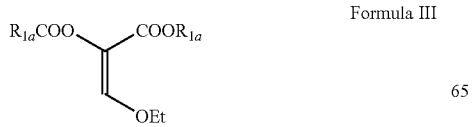

Formula III

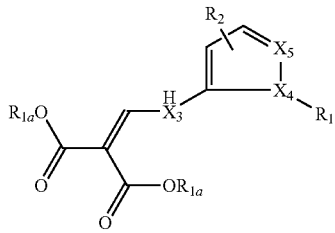

Formula IV (b) reacting the compound of Formula IV with phosphorous oxy halide to give a compound of Formula V (wherein $X_6$ is a halogen);

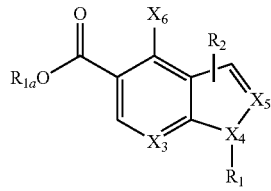

Formula V (c) reacting the compound of Formula V with a compound of Formula VI to give a compound of Formula VII (wherein $R_5$ and $R_6$ are the same as defined earlier);

Formula VI

R$_5$NHR$_6$

Formula VII

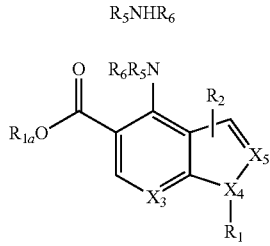

(d) performing ester hydrolysis on the compound of Formula VII to give a compound of Formula VIII;

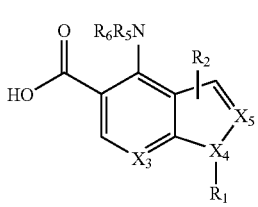

Formula VIII (e) reacting the compound of Formula VIII with a compound of Formula IX to give a compound of Formula X;

Formula IX

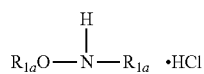

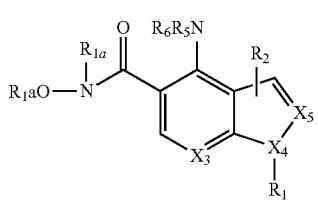
Formula X
(f) reduction of the compound of Formula X to give a compound of Formula XI;
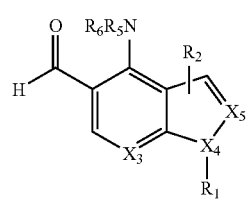
Formula XI
(g) reacting the compound of Formula XI with hydroxylamine hydrochloride to give a compound of Formula XII; and
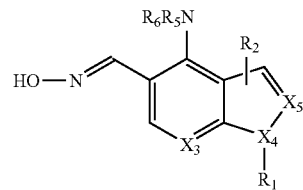
Formula XII
(h) reacting the compound of Formula XII with a compound of Formula XIII
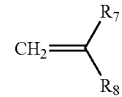
Formula XIII
to give a compound of Formula XIV.
\* \* \* \* \*

UNITED STATES PATENT AND TRADEMARK OFFICE
CERTIFICATE OF CORRECTION

| | | |
|---|---|---|
| PATENT NO. | : 7,915,286 B2 | Page 1 of 1 |
| APPLICATION NO. | : 12/067013 | |
| DATED | : March 29, 2011 | |
| INVENTOR(S) | : Venkata P. Palle | |

It is certified that error appears in the above-identified patent and that said Letters Patent is hereby corrected as shown below:

On the title page, item (75), inventor:
    change Sunanda Ghose Dastidar to -- Sunanda Ghosh Dastidar --

In the Specification

In Column 3, line 23:
    change allyl to -- alkyl --

In Column 5, line 40:
    change cyano, nitro, $COOR_\psi$, N-HC(=O)$R_\lambda$, -$NR_\lambda R_\pi$, to -- cyano, nitro, $COOR_\psi$, -NHC(=O)$R_\lambda$, -$NR_\lambda R_\pi$, --

In Column 10, line 2:
    change nitrites to -- nitriles --

Signed and Sealed this
Nineteenth Day of November, 2013

Teresa Stanek Rea
*Deputy Director of the United States Patent and Trademark Office*